(12) United States Patent
Guerret et al.

(10) Patent No.: US 8,450,380 B2
(45) Date of Patent: May 28, 2013

(54) METHOD FOR IMPLEMENTING ACTIVE INGREDIENTS IN ORDER TO PROTECT THEM AND OPTIMIZE THEIR DELIVERY METHOD

(75) Inventors: Olivier Guerret, La Tour de Salvagny (FR); Jean-Marc Suau, Lucenay (FR)

(73) Assignee: Coatex S.A.S., Genay (FR)

( * ) Notice: Subject to any disclaimer, the term of this patent is extended or adjusted under 35 U.S.C. 154(b) by 224 days.

(21) Appl. No.: 12/524,577

(22) PCT Filed: Jan. 30, 2008

(86) PCT No.: PCT/IB2008/000261
§ 371 (c)(1),
(2), (4) Date: Jul. 27, 2009

(87) PCT Pub. No.: WO2008/096237
PCT Pub. Date: Aug. 14, 2008

(65) Prior Publication Data
US 2010/0113617 A1    May 6, 2010

(30) Foreign Application Priority Data

Feb. 9, 2007  (FR) ..................................... 07 00926

(51) Int. Cl.
*A61K 47/32* (2006.01)
*A61K 9/14* (2006.01)
*A61K 9/50* (2006.01)
*C08F 20/30* (2006.01)
*C08F 20/28* (2006.01)

(52) U.S. Cl.
USPC ........... 514/772; 424/497; 424/489; 526/313; 526/318

(58) Field of Classification Search
USPC .................. 424/489, 497; 514/772; 526/313, 526/318
See application file for complete search history.

(56) References Cited

U.S. PATENT DOCUMENTS

| 4,384,096 | A | * | 5/1983 | Sonnabend | .................. 526/313 |
| 5,441,660 | A |   | 8/1995 | Tsaur et al. | |
| 6,372,259 | B1 | * | 4/2002 | Kumar | .......................... 424/497 |
| 2004/0030034 | A1 | * | 2/2004 | Chang et al. | .................. 524/543 |

FOREIGN PATENT DOCUMENTS
EP    1 331 262    7/2003

OTHER PUBLICATIONS

Kazuomi, Nagashima, V. Strashko, P. Macdonald, R. Jenkins, and D. Bassett. Diffusion of Model Hydrophobic Alkali-Swellable Emulsiohn Associative Thickeners, Macromolecules 2000, 33, 9329-9339.*

* cited by examiner

*Primary Examiner* — Fereydoun G Sajjadi
*Assistant Examiner* — Anna Falkowitz
(74) *Attorney, Agent, or Firm* — Oblon, Spivak, McClelland, Maier & Neustadt, L.L.P.

(57) ABSTRACT

The invention pertains to a new method for formulating pharmaceutical active ingredients in such a way as to protect them when ingested orally, and to allow for the controlling of the release of the active ingredient in the intestine. It relies upon the use of thickening acrylic emulsions with a pH greater than 5, containing hydrophobic groups, in order to encapsulate the pharmaceutical active ingredients for the purpose of encouraging their passage through the gastrointestinal barrier, while controlling the release kinetics of said active ingredients.

18 Claims, 1 Drawing Sheet

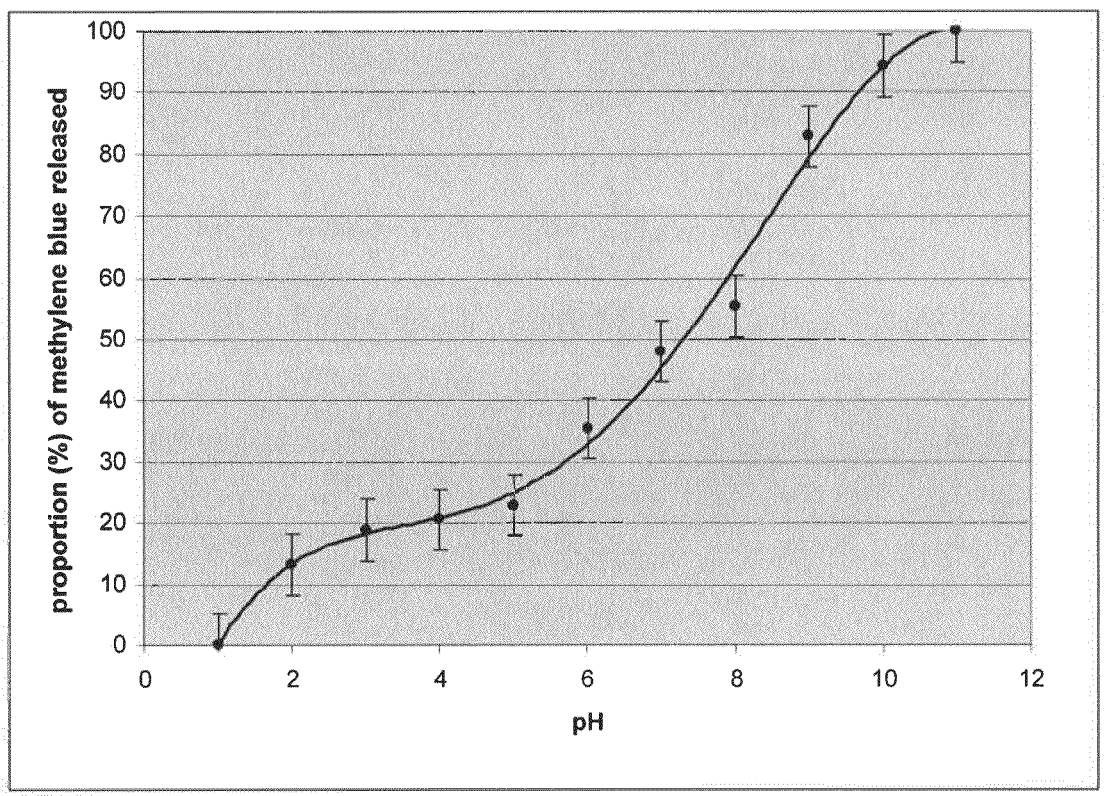

METHOD FOR IMPLEMENTING ACTIVE INGREDIENTS IN ORDER TO PROTECT THEM AND OPTIMIZE THEIR DELIVERY METHOD

This application is a 371 of PCT/IB2008/000261, filed Jan. 30, 2008.

SUMMARY OF THE INVENTION

The invention pertains to a new method for formulating pharmaceutical active ingredients in such a way as to protect them when ingested orally, and to allow for the controlling of the release of the active ingredient in the intestine. It relies upon the use of thickening acrylic emulsions with a pH greater than 5, containing hydrophobic groups, in order to encapsulate the pharmaceutical active ingredients for the purpose of encouraging their passage through the gastrointestinal barrier, while controlling the release kinetics of said active ingredients.

To that end, a first object of the invention is a method for manufacturing a formulation containing a pharmaceutical active ingredient, by mixing water, a HASE emulsion, and a pharmaceutical active ingredient, said mixture having a pH set to a value greater than 5. This mixture's pH may then be lowered to below 3: the result is a dispersion of solid particles in water, said particles being made up of a pharmaceutical active ingredient encapsulated inside polymer particles. Finally, this dispersion may be purified, with a view to obtaining solid particles, said particles being made up of a pharmaceutical active ingredient encapsulated inside polymer particles. A final object of the invention consists of the use of these aqueous formulations, these dispersions of solid particles in water, and these solid particles as agents with the dual function of protecting a pharmaceutical active ingredient in an acidic medium, and releasing it in a basic or alkaline medium.

The Applicant notes that the present Application is not intended to protect a therapeutic treatment method in any way. The present Application only pertains to a method for manufacturing formulations containing a pharmaceutical active ingredient, to the formulations thereby obtained, and to their use with the dual function of protecting a pharmaceutical active ingredient in an acidic medium and releasing it in a basic or alkaline medium: the function protected here is not in any way the therapeutic function of the active ingredient.

BACKGROUND DEFINITIONS

Pharmaceutical active ingredient: in the context of this invention, we use this term to refer to any substance with a therapeutic effect. For simplicity's sake, the Application may use the shortened expression "active ingredient" to refer to the "pharmaceutical active ingredient".

HASE: acronym for Hydrophobically Alkali Swellable Emulsion. This term refers to acrylic thickening agents based on (meth)acrylic acid, an ester of these acids, and a hydrophobic monomer.

TECHNICAL PROBLEM AND PRIOR ART

Although the activity of a pharmaceutical active ingredient is linked to its chemical structure, its effectiveness depends foremost on its concentration available to take effect inside the organism. This active ingredient's mode of dissemination within the organism is therefore a key factor in determining the effectiveness of a formula containing this active ingredient. The galenist will therefore choose a mode of administration that will make it possible to preserve the integrity of the active ingredient within the organism as much as possible.

Modes of administration are varied, but for the purpose of improving the patients' comfort, the preferred mode of administration is oral. However, the active ingredient must then pass through the gastro-intestinal barrier. If the active ingredient might be modified by chemical reactions that take place within the digestive system, the galenist must overdose the active ingredient within the formulation, which is not only economically negative, but may also lead to undesirable side effects. It is therefore important to provide the galenist with the means to protect the active ingredients in order to enable them to optimally pass through the gastro-intestinal barrier.

A method known to the person skilled in the art resides in the implementation of hydrophilic-hydrophobic block copolymers which lead to micellar core-shell structures that can enclose an active ingredient. The structures are particularly described in the document WO2004/112757, and react to the pH of the medium in which they are placed. These solutions are unsuitable, because they rely upon the implementation of solvents for incorporating a hydrophobic active ingredient within the micelles (in particular, see example 1 of the aforementioned document). However, the use of solvents poses problems from an industrial viewpoint (explosion hazards in workshops) and a sanitary viewpoint (potential traces of residual solvent).

Another method resides in the use of acrylic polymers, potentially manufactured as emulsions such as acrylic thickening emulsions better known by the term ASE (for Alkali Swellable Emulsion) in order to coat tablets containing the active ingredient. This coating dissolves in water at a high pH (from 5 to 7 depending on the structures), which enables the disintegration of the formula within the parts of the intestine which exhibit these pH conditions. Such polymers are commercially available under the names Eudragit™, or Kollicoat™, or Eastacryl 30D™. This method has the drawback of requiring that a tablet be prepared before coating it with a neutralized ASE solution. However, as the pharmaceutical active ingredients are often hydrophobic, they must often be formulated within a solvent before being incorporated into a tablet, and thus the aforementioned hazards arise.

One of the innovations of the inventive method is to use HASEs, which are unlike ASEs in that their structure contains an associative hydrophobic monomer. This monomer possesses the property, when the emulsion is thickened at a high pH, of creating associative hydrophobic interactions, which give a stronger thickening effect than with a polymer not containing such monomers. These hydrophobic nodules, whose size varies between 5 and 100 nanometers, are solvation cages of a hydrophobic active ingredient. The dilution of an active ingredient in a HASE solution is therefore made easier, and requires no use of an intermediary solvent.

The solutions thereby obtained, with an alkaline or slightly acidic pH (>5), are at risk of being destabilized by a change in pH. Thus, the passage of such a solution through the stomach, whose pH is close to 1, causes a phase separation of the polymers carrying the active ingredient within the polymer particles. This phase separation may correspond to precipitation when the glass transition temperature of the emulsion's polymer is high enough. When these particles travel through the intestine, they move from the duodenum (ph of 6) to the ileum (pH of 7.4). As this rise in pH occurs, said particles gradually attain a degree of water-solubility that enables the release of the active ingredient: this ingredient may then pass through the intestinal wall.

One of the Applicant's merits is having identified and used the phenomenon of water structure via a HASE emulsion, with a pH greater than 5: doing so naturally protects the active ingredients dissolved in this solution by breaking down the structure within the acidic medium of the stomach. The active ingredient is actually located in the core of the nanometric nodule within the precipitated polymer particles, these particles having micrometric sizes.

Such an implementation of HASE emulsions is, as far as we are currently aware, a new use of these objects, which were broadly described in applications for painting (see documents FR 2 693 203, FR 2 872 815, FR 2 633 930), the field of cosmetics (see the aforementioned document FR 2 872 815), or the cement industry (see the as-yet-unpublished French patent application with the docket number FR 07 00086). Furthermore, these technical fields are very far from the one pertaining to the present invention, and the aforementioned documents give no disclosures or instructions which could guide the person skilled in the art towards the present invention.

The description of the formulation may vary depending on the mixture's viscosity: for slightly thickened solutions, the formulation may be described as a syrup; for gelled formulations, these solutions may be fashioned in the form of capsules, for example.

Another advantage of the inventive method is delivering an active ingredient in a form that protects or releases it, depending on the pH of its environment; this form may be threefold:
  that of a liquid, which is an aqueous solution, when the product is prepared by only carrying out the inventive method's step of mixing at a pH greater than 5 (the precipitation then takes place within the patient's stomach),
  that of a liquid, which is a dispersion of solid particles in water, when the preparation of the product further implements the step of precipitation at a pH less than 3,
  that of a solid made up of solid particles of the active ingredient, which were trapped inside the polymer particles, when the inventive method's step of purification has been implemented.

DESCRIPTION OF THE INVENTION

A first object of the invention is therefore a method for manufacturing a formulation containing a pharmaceutical active ingredient, and characterized in that it comprises the steps of:
  a) mixing a HASE emulsion, a pharmaceutical active ingredient, and water, said mixture having a pH greater then 5, preferentially 6, and very preferentially 7,
  b) potentially precipitation by adjusting the pH to a value less than 3, preferentially 2, with a view to obtaining a dispersion of solid particles in water,
  c) potentially purification, with a view to obtaining the solid particles.

The inventive method is further characterized in that the pH of the mixture, during step a), is adjusted by means of an organic or mineral base. In practice, the components (the active ingredient, water, HASE emulsion, and the mineral or organic base) are added during agitation in a reactor; the order in which they are added will be chosen by the person skilled in the art, particularly based on the water-solubility of the active ingredient to be encapsulated.

The inventive method is further characterized in that during step a), 0.1% to 20%, preferentially 0.1% to 10%, and very preferentially 0.1% to 5% by dry weight of a HASE emulsion, in relation to the total weight of the aqueous formulation obtained after step a), is implemented.

The inventive method is further characterized in that during step a), 0.1% to 20% by dry weight of a hydrophobic or hydrophilic pharmaceutical active ingredient, in relation to the total weight of the aqueous formulation obtained after step a), is implemented.

The inventive method is further characterized in that a strong or somewhat strong is implemented during step b).

The inventive method is further characterized in that the HASE emulsion contains at least one copolymer of (meth)acrylic acid, a non-hydrosoluble monomer which is preferentially a (meth)acrylic ester chosen very preferentially from among ethyl acrylate, butyl acrylate, methyl methacrylate and mixtures thereof, and a monomer containing at least one hydrophobic group.

The inventive method is further characterized in that said monomer containing at least one hydrophobic group has the general formula:

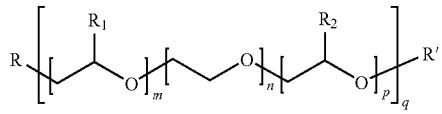

where:
  m, n, p and q are integers and m, n, p are less than 150,
  R has a polymerizable vinylic function,
  $R_1$ and $R_2$ are identical or different, and represent hydrogen atoms or alkyl groups,
  R' is a hydrophobic group comprising at least 6, preferentially at least 10, and very preferentially at least 12 carbon atoms.

The inventive method is further characterized in that the active ingredient is chosen from among pain relievers, and preferentially from among aspirin, ibuprofen, codeine or morphine, or is chosen from among withdrawal active ingredients and preferentially from among buprenorphine or methadone, or chosen from among antibiotics and preferentially from among penicillin, erythromycin, roxithromycin or telithromycin, or chosen from among anti-cancer medications and preferentially from among capecitabine or etoposide, or chosen from among the active ingredients used in the treatment of diabetes, and is preferentially insulin, or chosen from among the active ingredients used as antidepressants and is preferentially benzodiazepine, or chosen from among the active ingredients used in the treatment of gastric illnesses and is preferentially esomeprazole, or chosen from among the active ingredients used for controlling cholesterol and is preferentially simvastatin, or chosen from among the active ingredients used in the treatment of cardiovascular illnesses and preferentially from among lipitor or amlodipine, or chosen from among the active ingredients used in the treatment of mental illnesses and preferentially from among olanzapine or risperidone, or from mixtures of these active ingredients.

Another object of the invention is constituted by the aqueous formulation containing a pharmaceutical active ingredient, and obtained by implementing step a) of the method described above.

This aqueous formulation containing a pharmaceutical active ingredient is characterized:
  a) in that it contains water, a HASE emulsion and a pharmaceutical active ingredient,
  b) and in that it has a pH greater than 5, preferentially 6, and very preferentially 7.

This aqueous formulation is further characterized in that it contains 0.1% to 20%, preferentially 0.1% to 10%, and very preferentially 0.1% to 5% by dry weight of a HASE emulsion, in relation to its total weight.

This aqueous formulation is further characterized in that it contains 0.1% to 20%, by dry weight, of a hydrophilic or hydrophobic pharmaceutical active ingredient, in relation to its total weight.

This aqueous formulation is further characterized in that the HASE emulsion contains at least one copolymer of (meth) acrylic acid, a non-hydrosoluble monomer which is preferentially a (meth)acrylic ester chosen very preferentially from among ethyl acrylate, butyl acrylate, methyl methacrylate and mixtures thereof, and a monomer containing at least one hydrophobic group.

This aqueous formulation is further characterized in that said monomer containing at least one hydrophobic group has the general formula:

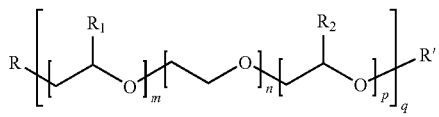

where:
- m, n, p and q are integers and m, n, p are less than 150,
- R has a polymerizable vinylic function,
- $R_1$ and $R_2$ are identical or different, and represent hydrogen atoms or alkyl groups,
- R' is a hydrophobic group comprising at least 6, preferentially at least 10, and very preferentially at least 12 carbon atoms.

This aqueous formulation is further characterized in that the active ingredient is chosen from among pain relievers, and preferentially from among aspirin, ibuprofen, codeine or morphine, or is chosen from among withdrawal active ingredients and preferentially from among buprenorphine or methadone, or chosen from among antibiotics and preferentially from among penicillin, erythromycin, roxithromycin or telithromycin, or chosen from among anti-cancer medications and preferentially from among capecitabine or etoposide, or chosen from among the active ingredients used in the treatment of diabetes, and is preferentially insulin, or chosen from among the active ingredients used as antidepressants and is preferentially benzodiazepine, or chosen from among the active ingredients used in the treatment of gastric illnesses and is preferentially esomeprazole, or chosen from among the active ingredients used for controlling cholesterol and is preferentially simvastatin, or chosen from among the active ingredients used in the treatment of cardiovascular illnesses and preferentially from among lipitor or amlodipine, or chosen from among the active ingredients used in the treatment of mental illnesses and preferentially from among olanzapine or risperidone, or from mixtures of these active ingredients.

Another object of the invention resides in the formulation made up of solid particles dispersed in water, and obtained by implementing the step of precipitation b) of the method described above.

This dispersion of solid particles in water is characterized in that the solid particles that make it up contain a pharmaceutical active ingredient and a copolymer of (meth)acrylic acid, a non-hydrosoluble monomer which is preferentially a (meth)acrylic ester chosen very preferentially from among ethyl acrylate, butyl acrylate, methyl methacrylate and mixtures thereof, and a monomer containing at least one hydrophobic group.

This dispersion of solid particles in water is further characterized in that said monomer containing at least one hydrophobic group has the general formula:

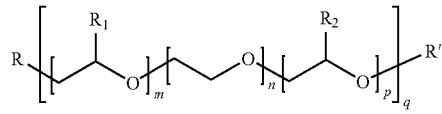

where:
- m, n, p and q are integers and m, n, p are less than 150,
- R has a polymerizable vinylic function,
- $R_1$ and $R_2$ are identical or different, and represent hydrogen atoms or alkyl groups,
- R' is a hydrophobic group comprising at least 6, preferentially at least 10, and very preferentially at least 12 carbon atoms.

This dispersion of solid particles in water is further characterized in that the active ingredient is chosen from among pain relievers, and preferentially from among aspirin, ibuprofen, codeine or morphine, or is chosen from among withdrawal active ingredients and preferentially from among buprenorphine or methadone, or chosen from among antibiotics and preferentially from among penicillin, erythromycin, roxithromycin or telithromycin, or chosen from among anti-cancer medications and preferentially from among capecitabine or etoposide, or chosen from among the active ingredients used in the treatment of diabetes, and is preferentially insulin, or chosen from among the active ingredients used as antidepressants and is preferentially benzodiazepine, or chosen from among the active ingredients used in the treatment of gastric illnesses and is preferentially esomeprazole, or chosen from among the active ingredients used for controlling cholesterol and is preferentially simvastatin, or chosen from among the active ingredients used in the treatment of cardiovascular illnesses and preferentially from among lipitor or amlodipine, or chosen from among the active ingredients used in the treatment of mental illnesses and preferentially from among olanzapine or risperidone, or from mixtures of these active ingredients.

Another object of the invention resides in the formulation made up of solid particles obtained by implementing the purification step c) of the method described above.

These solid particles are characterized in that they contain a pharmaceutical active ingredient and a copolymer of (meth) acrylic acid, a non-hydrosoluble monomer which is preferentially a (meth)acrylic ester chosen very preferentially from among ethyl acrylate, butyl acrylate, methyl methacrylate and mixtures thereof, and a monomer containing at least one hydrophobic group.

This formulation is further characterized in that said monomer containing at least one hydrophobic group has the general formula:

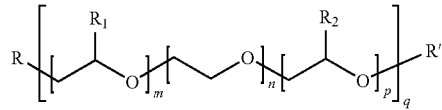

where:
- m, n, p and q are integers and m, n, p are less than 150,
- R has a polymerizable vinylic function,
- $R_1$ and $R_2$ are identical or different, and represent hydrogen atoms or alkyl groups,
- R' is a hydrophobic group comprising at least 6, preferentially at least 10, and very preferentially at least 12 carbon atoms.

These solid particles are further characterized in that the active ingredient is chosen from among pain relievers, and preferentially from among aspirin, ibuprofen, codeine or morphine, or is chosen from among withdrawal active ingredients and preferentially from among buprenorphine or methadone, or chosen from among antibiotics and preferentially from among penicillin, erythromycin, roxithromycin or telithromycin, or chosen from among anti-cancer medications and preferentially from among capecitabine or etoposide, or chosen from among the active ingredients used in the treatment of diabetes, and is preferentially insulin, or chosen from among the active ingredients used as antidepressants and is preferentially benzodiazepine, or chosen from among the active ingredients used in the treatment of gastric illnesses and is preferentially esomeprazole, or chosen from among the active ingredients used for controlling cholesterol and is preferentially simvastatin, or chosen from among the active ingredients used in the treatment of cardiovascular illnesses and preferentially from among lipitor or amlodipine, or chosen from among the active ingredients used in the treatment of mental illnesses and preferentially from among olanzapine or risperidone, or from mixtures of these active ingredients.

A final object of the invention is the use of the aqueous formulations of a pharmaceutical active ingredient, the aqueous dispersions of solid particles of a pharmaceutical active ingredient, and the solid particles of a pharmaceutical active ingredient, as an agent with the dual function of protecting a pharmaceutical active ingredient in an acidic medium and releasing it into a basic or alkaline medium.

EXAMPLES

Example 1

This example illustrates the inventive method, wherein an aqueous formulation of a pharmaceutical active ingredient, which is methylene blue, is first created in accordance with step a), in the presence of various HASE emulsions, at a pH greater than 5. Methylene blue is soluble in water and organic solvents, and its color makes it recognizable whether it is encapsulated inside polymer particles or is released in water. These formulations are then precipitated in accordance with step b) of the inventive method, by lowering the pH to a value less than 3: this shows how the methylene blue becomes trapped within the polymer particles.

Finally, they are placed into a medium where the pH is increased, so as to demonstrate that the methylene blue is then gradually released as the pH increases.

This example therefore illustrates the various objects of the invention and their use as agents for protecting an active ingredient in an acidic environment and for releasing it in a basic or alkaline environment.

Manufacturing the Aqueous Formulations 3.33 g of a HASE emulsion, with 30% solids content, is weighed out. 100 g of a water solution containing 130 ppm of methylene blue is added. The medium is agitated during this addition, and the pH is set to a value greater than 5 using a sodium hydroxide solution. A control containing no HASE is also manufactured by mixing 0.013 g of methylene blue in 100 mL of water: its pH is also set to a value greater than 5 by adding a sodium hydroxide solution.

The tests according to the invention are characterized by the choice of emulsion, the Brookfield™ viscosities of the formulation at 10 and 100 revolutions per minute (respectively denoted $\mu_{10}$ and $\mu_{100}$) at 25° C.: the ratio of these viscosities is characteristic of HASE emulsions, and depends upon the hydrophobic groups chosen, as well as the monomer ratios, with the viscosity achieved being a function of the quantity of the HASE emulsion used. These results are given in Table 1.

TABLE 1

| Test no. | HASE Emulsion | pH | $\mu_{10}$ (mPa · s) | $\mu_{100}$ (mPa · s) |
|---|---|---|---|---|
| control | — | 9.0 | 0 | 0 |
| 1 | Rhéo ™ 2000 | 9.6 | 40 | 20 |
| 2 | Rhéo ™ 2100 | 9.5 | 40 | 20 |
| 3 | Rhéo ™ 3000 | 9.1 | 1000 | 340 |
| 4 | Rhéo ™ 3800 | 7.3 | 1060 | 2300 |
| 5 | Thixol ™ 53L | 7.4 | 5200 | 32000 |
| 6 | Viscoatex ™ 730 | 11.2 | 790 | 3900 |
| 7 | Acrysol ™ TT935 | 7.45 | 60 | 100 |
| 8 | Acrysol ™ TT615 | 11.9 | 1210 | 7800 |

The polymers of tests 1 to 6 are acrylic HASE thickening agents sold by the company COATEX, and the polymers of tests 7 and 8 are HASE emulsions sold by the company ROHM & HAAS.

All inventive aqueous formulations are transparent and uniformly blue, and the viscosities recorded confirm the presence of gels (compared with the control formulation). The dimensions of these methylene blue solvation cages are on the order of a few tens of nanometers, because the light is not diffracted by this solution. Their distribution is homogeneous, as the uniformity of the blue coloring indicates.

Co-precipitation of Aqueous Formulations

The concentration of methylene blue in water is determined using a UV spectrometer, measuring the adsorption intensity at a wavelength of 652 nm. The control is used to calibrate the device: the percentage of light that it absorbs is set to 100%.

40 g of each of the solutions corresponding to tests #1 to #8 are sampled, as is 40 g of the control solution. These 40 g are poured, one drop at a time, onto a 15% solution of phosphoric acid, so that the final pH of the aqueous phase is equal to 1.2.

For tests #1 to #8, a phase separation is observed: blue particles are formed, and the supernatants are very lightly colored. The control, on the other hand, maintains a uniform blue color.

The size of the particles obtained was measured through dynamic light scattering using a Zetasizer™ Nano S90 sold by the company MALVERN™ (see table 2).

TABLE 2

| Test no. | HASE Emulsion | Particle size (nm) |
|---|---|---|
| 1 | Rhéo ™ 2000 | 340 |
| 2 | Rhéo ™ 2100 | 800 |
| 3 | Rhéo ™ 3000 | 1260 |
| 4 | Rheo ™ 3800 | 4510 |
| 5 | Thixol ™ 53L | 930 |
| 6 | Viscoatex ™ 730 | 3200 |

Release of Methylene Blue Stimulated by pH

The suspension obtained during test #2 is then used to demonstrated that in a context of rising pH, the polymer particles which trapped the methylene blue release the active ingredient. A 5% solution of sodium hydroxide is therefore added one drop at a time, while keeping the suspension agitated. The dosage is carried out using addition kinetics corresponding to an increase of one pH unit per hour. This neutralization simulates the progress of a product moving from the stomach (pH=1) to the ileum (pH=7.4).

As the neutralization is taking place, the supernatant is analyzed using refractometry: the relative quantity of methylene blue in relation to the target quantity is thereby determined. FIG. 1/1 represents the proportion of methylene blue released, as a function of pH. This demonstrates the ability of the vesicles formed to release their active ingredient as a function of the pH of the medium into which they are dispersed.

Example 2

This example illustrates the inventive method, wherein the pharmaceutical active ingredient is 2,9 dichloro-5,12 dihydroquino [2,3-b] acridine-7,14 dione or 2,6 dichloquinacridone sold by the company CIBA GEIGY™ under the name Magenta Cinquasia RT-235-D. This is a non-hydrosoluble coloring. Its red color makes it easy to tell whether or not the molecule is present in water.

Manufacturing the Aqueous Formulations 3.33 g of a HASE emulsion sold by the company COATEX under the name Thixol™ 53L, whose dry solids content is 30% of its weight, is weighed out. 100 g of a solution of water and 0.015 g of this coloring is added during agitation. The coloring remains in a dispersed form.

The medium is then neutralized with a 20% solution of sodium hydroxide until it reaches pH 9, and a gel is obtained in which the dispersed coloring powder is ultimately fully incorporated into the formulation until a homogeneous red solution is obtained, free from all insoluble particles.

Brookfield™ viscosities are obtained at 10 and 100 revolutions per minute and at 25° C., these being respectively equal to 13,000 mPa·s and 1,900 mPa·s.

Co-Precipitation

A 15% solution of phosphoric acid is then added, so as to obtain a pH equal to 2.4.

A phase separation is observed. Red particles form. The supernatants become very lightly colored.

The invention claimed is:

1. A method for manufacturing a formulation comprising a pharmaceutical active ingredient, comprising:
   a) mixing a Hydrophobically Alkali Swellable Emulsion (HASE), a pharmaceutical active ingredient, and water to produce a mixture, said mixture having a pH greater than 5,
   b) optionally precipitating from said mixture, by adjusting the pH to a value less than 3, a dispersion of solid particles in water,
   c) optionally purifying the solid particles,
   wherein the HASE comprises at least one copolymer of (meth)acrylic acid, a non-hydrosoluble monomer and a monomer comprising at least one hydrophobic group of the formula:

$$R\left[\begin{array}{c}R_1\\ \phantom{x}\\ \phantom{x}\\ O\end{array}\right]_m\left[\phantom{x}O\phantom{x}\right]_n\left[\begin{array}{c}R_2\\ \phantom{x}\\ \phantom{x}\\ O\end{array}\right]_p{}_q R'$$

where:
   m, n, p and q are integers and m, n, p are less than 150,
   R has a polymerizable vinylic function,
   $R_1$ and $R_2$ are identical or different, and represent hydrogen atoms or alkyl groups, and
   R' is a hydrophobic group comprising at least 6 carbon atoms.

2. The method according to claim 1, wherein the mixture's pH during a) is adjusted by an organic or mineral base.

3. The method according to claim 1, wherein 0.1% to 20%, by dry weight of a HASE, in relation to the total weight of the aqueous formulation obtained after a), is implemented.

4. The method according to claim 1, wherein during a), 0.1% to 20% by dry weight of a hydrophobic or hydrophilic pharmaceutical active ingredient, in relation to the total weight of the aqueous formulation obtained after a), is implemented.

5. The method according to claim 1, wherein an acid is implemented during b).

6. The method according to claim 1, wherein the non-hydrosoluble monomer is selected from the group consisting of ethyl acrylate, butyl acrylate, methyl methacrylate and mixtures thereof.

7. The method according to claim 1, wherein the active ingredient is a pain reliever, a withdrawal active ingredient, an antibiotic, an anti-cancer medication, an active ingredient used in the treatment of diabetes, an active ingredient used as an antidepressant, an active ingredient used in the treatment of gastric illnesses, an active ingredient used for controlling cholesterol, an active ingredient used in the treatment of cardiovascular illnesses, an active ingredient used in the treatment of mental illnesses, or a mixture thereof.

8. An aqueous formulation comprising a pharmaceutical active ingredient wherein:
   a) the formulation comprises water, a HASE and a pharmaceutical active ingredient,
   b) the formulation has a pH greater than 5
   wherein the HASE comprises at least one copolymer of (meth)acrylic acid, a non-hydrosoluble monomer and a monomer comprising at least one hydrophobic group of the formula:

$$R\left[\begin{array}{c}R_1\\ \phantom{x}\\ O\end{array}\right]_m\left[\phantom{x}O\phantom{x}\right]_n\left[\begin{array}{c}R_2\\ \phantom{x}\\ O\end{array}\right]_p{}_q R'$$

where:
   m, n, p and q are integers and m, n, p are less than 150,
   R has a polymerizable vinylic function,
   $R_1$ and $R_2$ are identical or different, and represent hydrogen atoms or alkyl groups, and
   R' is a hydrophobic group comprising at least 6 carbon atoms.

9. The aqueous formulation according to claim 8, wherein the formulation comprises 0.1% to 20% by dry weight of a HASE, in relation to the total weight.

10. The aqueous formulation according to claim 8, wherein the formulation comprises 0.1% to 20%, by dry weight, of a hydrophilic or hydrophobic pharmaceutical active ingredient, in relation to the total weight.

11. The aqueous formulation according to claim 8, wherein the non-hydrosoluble monomer is selected from the group consisting of ethyl acrylate, butyl acrylate, methyl methacrylate and mixtures thereof.

12. The aqueous formulation according to 8, wherein the active ingredient is a pain reliever, a withdrawal active ingredient, an antibiotic, an anti-cancer medication, an active ingredient used in the treatment of diabetes, an active ingredient used as antidepressants, an active ingredient used in the treatment of gastric illnesses, an active ingredient used for controlling cholesterol, an active ingredient used in the treatment of cardiovascular illnesses, an active ingredient used in the treatment of mental illnesses, or a mixture thereof.

13. A dispersion of solid particles in water, wherein the solid particles comprise a pharmaceutical active ingredient and a copolymer of (meth)acrylic acid, a non-hydrosoluble monomer, and a monomer comprising at least one hydrophobic group,
wherein the monomer comprising at least one hydrophobic group is a monomer of the formula:

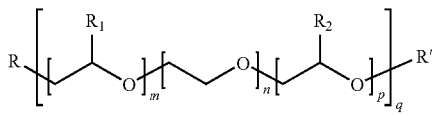

where:
m, n, p and q are integers and m, n, p are less than 150,
R has a polymerizable vinylic function,
$R_1$ and $R_2$ are identical or different, and represent hydrogen atoms or alkyl groups, and
R' is a hydrophobic group comprising at least 6 carbon atoms.

14. The dispersion of solid particles according to claim 13, wherein the active ingredient is a pain reliever, a withdrawal active ingredient an antibiotic, an anti-cancer medication, an active ingredient used in the treatment of diabetes, an active ingredient used in the treatment of gastric illnesses, an active ingredient used for controlling cholesterol, an active ingredient used in the treatment of cardiovascular illnesses, an active ingredient used in the treatment of mental illnesses, or a mixture thereof.

15. A solid particle comprising a pharmaceutical active ingredient and a copolymer of (meth)acrylic acid, a non-hydrosoluble monomer, and a monomer comprising at least one hydrophobic group,
wherein the monomer comprising at least one hydrophobic group is a monomer of the formula:

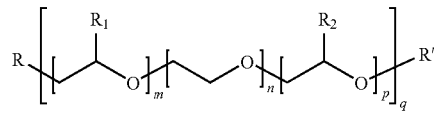

where:
m, n, p and q are integers and m, n, p are less than 150,
R has a polymerizable vinylic function,
$R_1$ and $R_2$ are identical or different, and represent hydrogen atoms or alkyl groups, and
R' is a hydrophobic group comprising at least 6 carbon atoms.

16. The solid particle according to claim 15, wherein the active ingredient is a pain reliever, a withdrawal active ingredient, an antibiotic, an anti-cancer medication, an active ingredient used in the treatment of diabetes, an active ingredient used as antidepressants, an active ingredient used in the treatment of gastric illnesses, an active ingredient used for controlling cholesterol, an active ingredient used in the treatment of cardiovascular, an active ingredient used in the treatment of mental illnesses, or a mixture thereof.

17. An agent comprising the aqueous formulation according to claim 8 with a dual function of protecting a pharmaceutical active ingredient in an acidic medium and releasing the ingredient into a basic or alkaline medium.

18. The method according to claim 1, comprising precipitating from said mixture, by adjusting the pH to a value less than 3, a dispersion of solid particles in water.

* * * * *